(12) United States Patent
Matsushita

(10) Patent No.: US 8,287,807 B2
(45) Date of Patent: Oct. 16, 2012

(54) ANALYZER AND COMMUNICATION METHOD

(75) Inventor: Atsushi Matsushita, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 465 days.

(21) Appl. No.: 12/325,826

(22) Filed: Dec. 1, 2008

(65) Prior Publication Data

US 2009/0087915 A1   Apr. 2, 2009

Related U.S. Application Data

(63) Continuation of application No. PCT/JP2007/061065, filed on May 31, 2007.

(30) Foreign Application Priority Data

May 31, 2006   (JP) .................................. 2006-152590

(51) Int. Cl.
*G01N 35/00*   (2006.01)
(52) U.S. Cl. ................ 422/67; 422/63; 422/64; 436/43; 436/50; 436/55; 702/19; 703/25
(58) Field of Classification Search ........................ None
See application file for complete search history.

(56) References Cited

U.S. PATENT DOCUMENTS

| 6,444,171 | B1 * | 9/2002 | Sakazume et al. ............... 422/65 |
| 2004/0034478 | A1 * | 2/2004 | Yung et al. ...................... 702/19 |
| 2006/0148063 | A1 * | 7/2006 | Fauzzi et al. ............... 435/286.4 |
| 2007/0237675 | A1 * | 10/2007 | Nichols et al. ................. 422/63 |

FOREIGN PATENT DOCUMENTS

| JP | 04-262594 | 9/1992 |
| JP | 06-319184 | 11/1994 |
| JP | 09-274044 | 10/1997 |
| JP | 11-233974 | 8/1999 |
| JP | 2000-156998 | 6/2000 |

* cited by examiner

*Primary Examiner* — P. Kathryn Wright
(74) *Attorney, Agent, or Firm* — Kilpatrick Townsend & Stockton LLP

(57) ABSTRACT

An analyzer for analyzing a specimen includes a central control unit that instructs systems of the analyzer of a process operation; and a primary control unit that time-divisionally outputs an instruction by the central control unit. The analyzer also includes a plurality of secondary control units; a communication connection unit; and a plurality of connecting units. The secondary control units are connected to the systems, respectively, and control an operation of the systems according to the instruction by the central control unit. Each of the secondary control units has positional information set in advance. The communication connection unit connects the primary control unit and the secondary control units. The connecting units are provided on a fixed arrangement position, have arrangement positional information indicating the arrangement position, and are connected to the secondary control units, respectively.

5 Claims, 13 Drawing Sheets

US 8,287,807 B2

ANALYZER AND COMMUNICATION METHOD

CROSS-REFERENCE TO RELATED APPLICATIONS

This application is a continuation of PCT international application Ser. No. PCT/JP2007/061065 filed on May 31, 2007 which designates the United States, incorporated herein by reference, and which claims the benefit of priority from Japanese Patent Application No. 2006-152590, filed on May 31, 2006, incorporated herein by reference.

BACKGROUND OF THE INVENTION

1. Field of the Invention

The present invention relates to an analyzer for analyzing a specimen, and a communication method in the analyzer.

2. Description of the Related Art

Conventionally, as a device for automatically analyzing a specimen such as blood and body fluid, an analyzer in which the specimen is added to a reaction vessel to which a reagent is dispensed and a reaction generated between the reagent and the specimen in the reaction vessel is optically detected is known. In such an analyzer, a plurality of control boards each controlling each unit for dispensing, stirring, measuring light, and cleaning, and a main control unit for instructing each unit of a process operation are connected through a predetermined network line. In the analyzer, the main control unit and each control board communicate to each other through the network line to dispense the specimen and the reagent, stir liquid in the reaction vessel, measure light, and clean the reaction vessel of which light measuring is finished (refer to Japanese Patent Application Laid-open No. 09-274044).

SUMMARY OF THE INVENTION

An analyzer according to an aspect of the present invention is for analyzing a specimen and includes a central control unit that instructs systems of the analyzer of a process operation; and a primary control unit that time-divisionally outputs an instruction by the central control unit. The analyzer also includes a plurality of secondary control units; a communication connection unit; and a plurality of connecting units. The secondary control units are connected to the systems, respectively, and control an operation of the systems according to the instruction by the central control unit. Each of the secondary control units has positional information set in advance. The communication connection unit connects the primary control unit and the secondary control units. The connecting units are provided on a fixed arrangement position, have arrangement positional information indicating the arrangement position, and are connected to the secondary control units, respectively.

A communication method according to another aspect of the present invention is for an analyzer including a plurality of control units which are connected to systems, respectively, controls an operation of the systems, and each of which has positional information set in advance, and a plurality of connecting units which are provided on a fixed arrangement position have arrangement positional information indicating the arrangement position, and are connected to the control units. The communication method includes obtaining the positional information in each of the control units being a communication object; obtaining the arrangement positional information in each of the connecting units which is connected to the control unit being the communication object; and determining whether the positional information obtained and the arrangement positional information obtained match. When it is determined that the positional information and the arrangement positional information match, communication in the control unit being the communication object is allowed.

A computer program product according to still another aspect of the present invention has a computer readable medium including programmed instructions for performing the communication method according to the present invention.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
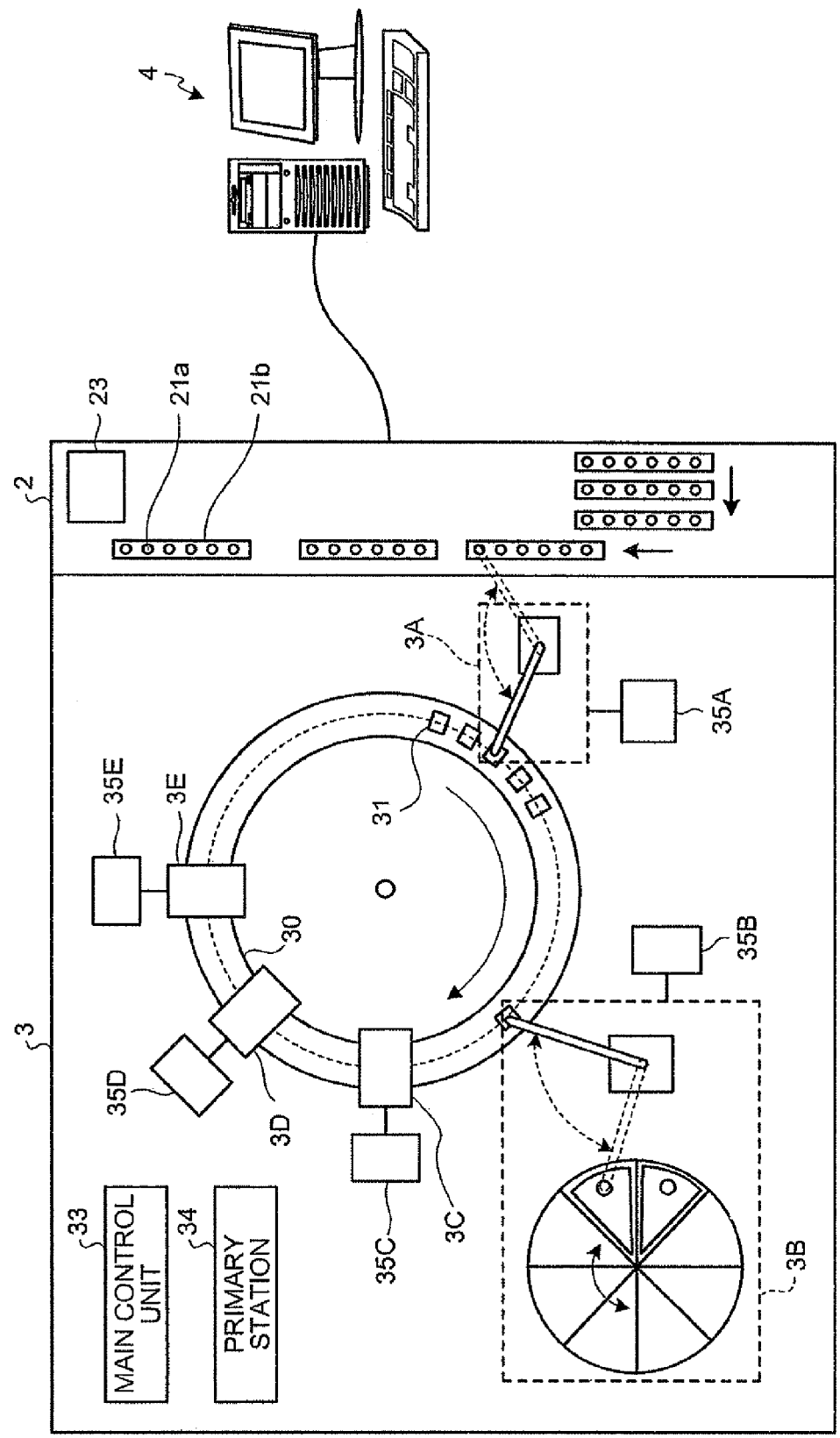
FIG. 1 is a schematic view showing a configuration of an analyzer according to a first embodiment.

Hereinafter, an analyzer according to an embodiment of the present invention is described with reference to the drawings. Meanwhile, the invention is not limited by this embodiment. In addition, the same reference numeral is given to the same portion in the drawings.

First, a first embodiment is described. FIG. 1 is a schematic view showing a configuration of an analyzer according to the first embodiment. As shown in FIG. 1, an analyzer 1 according to the first embodiment is provided with a transfer system 2 for transferring a specimen being an analysis object, a measuring system 3 for optically measuring the specimen, and a management device 4 for managing a process operation of the transfer system 2 and the measuring system 3 and performing an analysis process, and the systems cooperate with each other to automatically analyze a plurality of specimens biochemically, immulogically, or genetically. The transfer system 2 and the measuring system 3 are linked to the management device 4 by wired or wireless connection. Meanwhile, the analyzer 1 may have a plurality of measuring systems 3.

The transfer system 2 is provided with a plurality of specimen racks 21b for holding a plurality of specimen vessels 21a accommodating liquid specimen such as blood and urine and sequentially transfer them in a direction indicated by an arrow in the drawing. The specimen in a specimen vessel 21a transferred to a predetermined position on the transfer system 2 is dispensed to a reaction vessel 31 delivered while being arranged on a reaction table 30 by a specimen dispensing unit 3A in the measuring system 3. Each process operation of each component of the transfer system 2 is controlled by a main control unit 23, based on an instruction transmitted from the management device 4.

The measuring system 3 has the reaction table 30, the specimen dispensing unit 3A, a reagent dispensing unit 3B, a stirring unit 3C, a light measuring unit 3D, and a cleaning unit 3E. The reaction table 30 transfers the reaction vessel 31 to a predetermined position for dispensing the specimen and a reagent to the reaction vessel 31, and for stirring and cleaning the reaction vessel 31 or measuring light thereof. The specimen dispensing unit 3A sucks in the specimen from the specimen vessel 21a transferred to the predetermined position on the transfer system 2 and discharges and dispenses the specimen to the reaction vessel 31. The reagent dispensing unit 3B sucks in the reagent from a reagent vessel in a reagent chamber transferred to the predetermined position and discharges and dispenses the reagent to the reaction vessel 31. The stirring unit 3C stirs the specimen and the reagent dispensed to the reaction vessel 31 to facilitate a reaction. The light measuring unit 3D emits light to the reaction vessel 31 conveyed to a predetermined light measuring position and receives the light, which has passed through the liquid in the reaction vessel 31, to measure intensity thereof. A measurement result by the light measuring unit 3D is output to the management device 4 for an analysis process on the specimen. The cleaning unit 3E cleans the inside of the reaction vessel 31 of which measurement by the light measuring unit 3D is finished. Although the cleaned reaction vessel 31 is reused, this may be disposed after a single measurement depending on contents of examination.

The measuring system 3 has a main control unit 33, a primary station 34, and secondary stations 35A to 35E connected to units 3A to 3E, respectively. The main control unit 33 transmits instruction information for instructing each unit composing the measuring system 3 of a process operation, based on the instruction transmitted from the management device 4, and controls the process operation in each component of each unit of the measuring system 3. The primary station 34 is linked to the main control unit 33 by a wired connection to time-divisionally output the instruction by the main control unit 33 to the secondary stations 35A to 35E connected to each unit. The primary station 34 controls a communication process in a network 37 to be described later, and has a function as an interface between the main control unit 33 and each of the secondary stations 35A to 35E. By providing the primary station 34 between the main control unit 33 and each of the secondary stations 35A to 35E, it is not required that the main control unit 33 directly transmits the instruction information to each of the secondary stations 35A to 35E, so that a load on the main control unit 33, which controls an entire measuring system 3, may be reduced. Meanwhile, the main control unit 33 and the primary station 34 may be linked by a wireless connection.

Each of the secondary stations 35A to 35E controls an operation of each connected unit according to the instruction by the main control unit 33 output by the primary station. The secondary station 35A is connected to the specimen dispensing unit 3A to control the operation of each component of the specimen dispensing unit 3A. The secondary station 35B is connected to the reagent dispensing unit 3B to control the operation of each component of the reagent dispensing unit 3B. The secondary station 35C is connected to the stirring unit 3C to control the operation of each component of the stirring unit 3C. The secondary station 35D is connected to the light measuring unit 3D to control the operation of each component of the light measuring unit 3D. The secondary station 35E is connected to the cleaning unit 3E to control the operation of each component of the cleaning unit 3E. Each of the secondary stations 35A to 35E has positional information indicating a position on which each of the secondary stations 35A to 35E should be disposed and the positional information set in advance with respect to each of secondary station substrates 35A to 35E. Meanwhile, although not shown, the reaction table 30 also is connected to a predetermined secondary station 35 in a similar manner, and the reaction table 30 performs a transfer process of the reaction vessel 31 by control by the connected secondary station 35.

Figure 2:
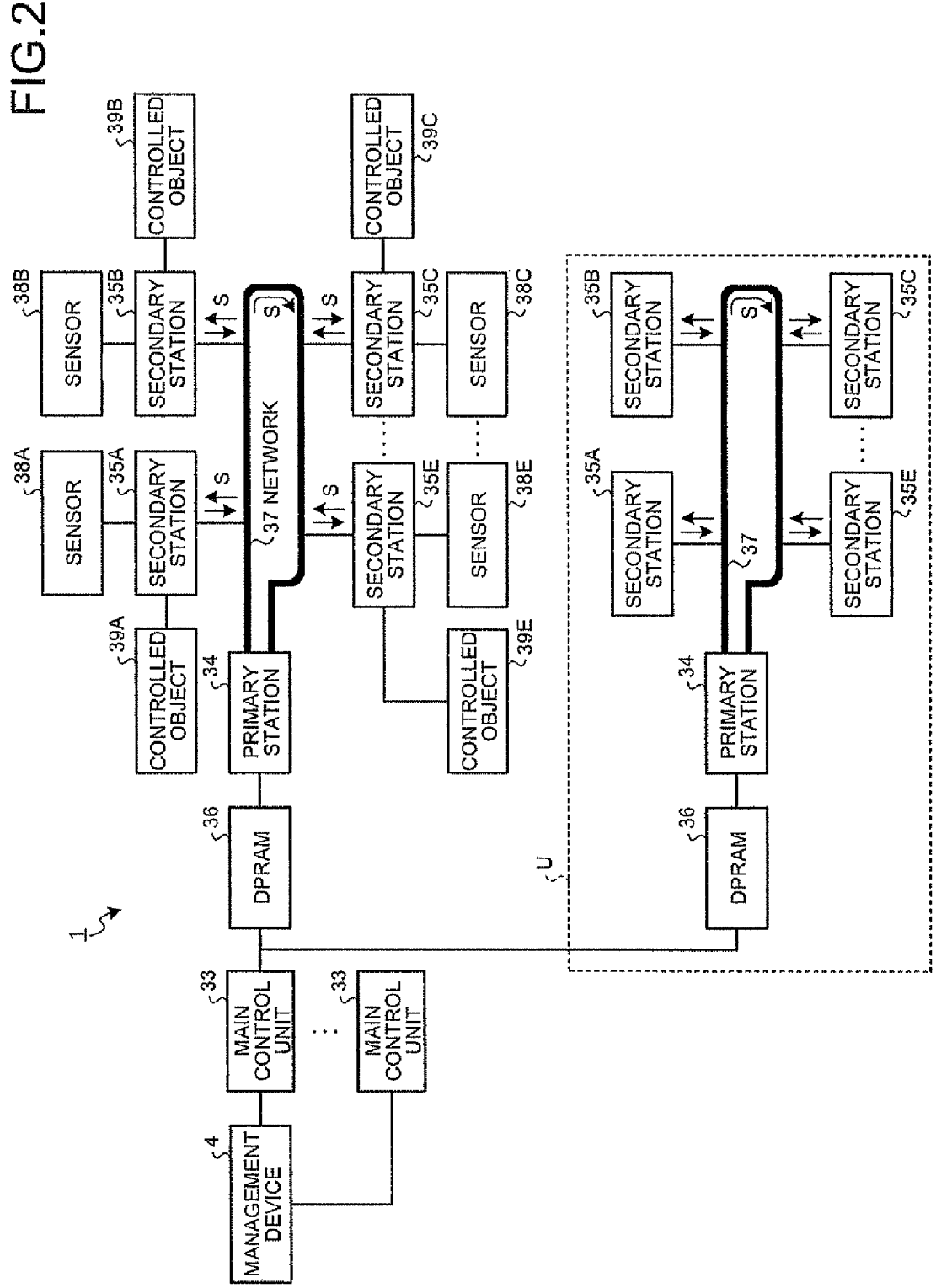
FIG. 2 is a view illustrating a connection state of each component composing the analyzer shown in FIG. 1.

Next, a connection status of each component composing the analyzer 1 is described with reference to FIG. 2. FIG. 2 shows the connection status between the measuring system 3 and the management device 4 in order to simplify the description.

As shown in FIG. 2, in the analyzer 1, each main control unit 33 in each measuring system 3 is connected to the management device 4. In order to efficiently transfer information and a parameter, a DPRAM 36 is provided between the main control unit 33 and the primary station 34. The main control unit 33 and the DPRAM 36 are connected to each other through a predetermined line, and the DPRAM 36 and the primary station 34 also are connected to each other through the predetermined line in a similar manner.

Also, the primary station 34 and each of the secondary stations 35A to 35E are connected through the network 37. The secondary stations 35A and 35E are connected to sensors 38A to 38E and controlled objects 39A to 39E composing each unit to control the process operations of the sensors 38A to 38E and the controlled objects 39A to 39E. For example, as the sensors 38A to 38E, there is a sensor for detecting the position of the specimen vessel 21a or the reaction vessel 31 being the detection object by detecting whether the specimen vessel 21a or the reaction vessel 31 is transferred within a detection range. For example, as the controlled object 39A, there is a suction/discharge system in the specimen dispensing unit 3A, and a transfer system to transfer the suction/discharge system on the specimen vessel 21a or the reaction vessel 31 and to move up and down the suction/discharge system in a vertical direction. Meanwhile, in the measuring system 3, it is possible to build an additional unit U having the DPRAM 36, the primary station 34, each of the secondary stations 35A to 35E, and the network 37, thereby flexibly expanding the device.

Each of the secondary stations 35A to 35E obtains position detection information indicating the position of the detection object detected by the sensors 38R to 38E connected to them, respectively, and operational information regarding the process operations of the controlled objects 39A to 39E connected to them, respectively. Each of the secondary stations 35A to 35E transmits a signal S corresponding to the position detection information and the operational information to the primary station 34 through the network 37. The signal S transmitted from each of the secondary stations 35A to 35E is transmitted to the main control unit 33 through the primary station 34 and the DPRAM 36, and the main control unit 33 determines whether the process operation of each unit to which the secondary stations 35A to 35E are connected has abnormality, based on the received signal S.

Also, each of the secondary stations 35A to 35E transmits and receives the signal S to/from another one of the secondary stations 35A to 35E through the network 37. Specifically, the secondary stations 35A to 35E may directly transmit the signal S to another one of the secondary stations 35A to 35E being a destination or may transmit the signal S through the primary station 34. Specifically, each of the secondary stations 35A to 35E transmits information specifying any one of the secondary stations 35A to 35E being the destination to the primary station 34 together with the signal S, and based on the received information, the primary station 34 specifies any of the secondary stations 35A to 35E being the destination to transmit the signal S.

Figure 3:
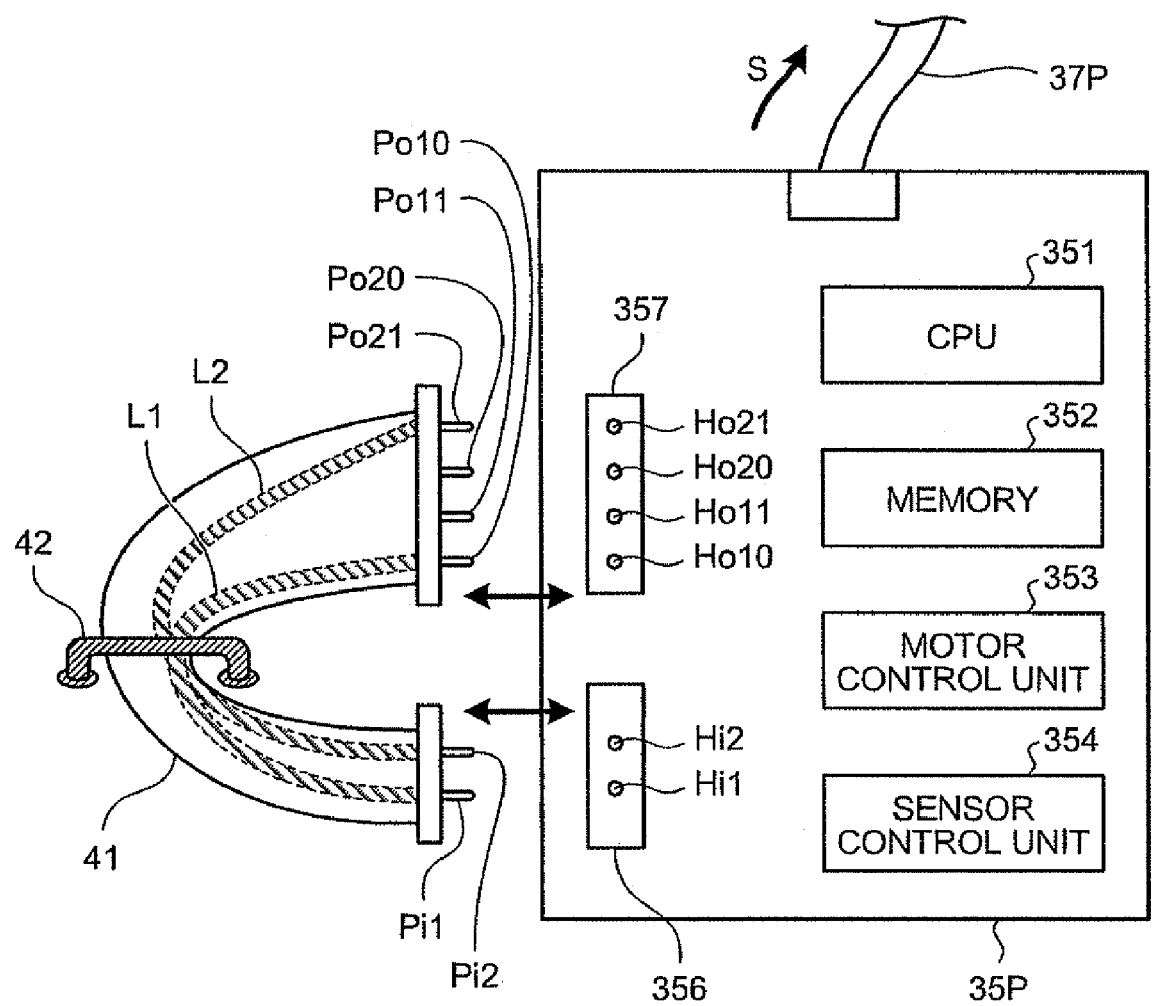
FIG. 3 is a view illustrating an arrangement of a secondary station substrate composing a secondary station shown in FIG. 2.

Next, an arrangement of a secondary station board composing each of the secondary stations 35A to 35E is described with reference to FIG. 3. The secondary station board composing each of the secondary stations 35A to 35E is provided with a CPU 351, a memory 352, a motor control unit 353, and a sensor control unit 354, as a secondary station board 35P shown in FIG. 3, and any secondary station board composing each of the secondary stations 35A to 35E has a similar hardware configuration. By using the secondary station board 35P having the similar hardware configuration, the analyzer 1 may build a versatile device configuration. In the secondary station board 35P, the CPU 351 controls a process and an operation of each part of the secondary station board 35P, the memory 352 stores information regarding the process operation of the sensor connected to the secondary station board 35P and the controlled object and a program or the like incorporated in the secondary station board 35P, the motor control unit 353 controls a motor for driving the controlled object connected to the secondary station board 35P, and the sensor control unit 354 controls the sensor connected to the secondary station board 35P. In each of the secondary station boards 35P having the similar hardware configuration, the program is set up according to the sensor connected to the secondary station board 35P and the controlled object.

Also, each of the secondary station board 35P has the positional information indicating the position on which the secondary station board 35P should be arranged. The positional information is set in advance corresponding to the position on which the secondary station board 35P should be arranged, and is stored in the memory 352 in each of the secondary station boards 35P. Also, the positional information is used in the instruction to each secondary station 35 by the main control unit 33 and information transmission by the primary station 34 to each secondary station 35.

Further, the secondary station board 35P has an input connector 356 provided with jacks Hi1 and Hi2 to and from which the pin of an input side of a check cable to be described later may be inserted and removed, and an output connector 357 provided with jacks Ho10, Ho11, Ho20 and Ho21 to and from which a pin of an output side of the check cable may be inserted and removed.

In the analyzer 1, a check cable 41 is provided near the position on which each of the secondary station board 35P should be arranged. The arrangement position of the check cable 41 is fixed by a fixing member 42. In addition, a cable length of the check cable 41 is set in advance and may not be changed. The pin, which may be inserted to and removed from the jack of the input connector 356 of the secondary station board 35P, is provided on one end of the check cable 41. The pin, which may be inserted to and removed from the jack of the output connector 357 of the secondary station board 35P, is provided on the other end of the check cable 41. The arrangement position of the check cable 41 is fixed, and the cable length thereof may not be changed, so that the check cable 41 may be connected only to the secondary station board 35P arranged on the predetermined position near the check cable 41, as shown in FIG. 3.

Pins Pi1 and Pi2 are provided on the end of the check cable 41 corresponding to the input connector 356. The pin Pi1 is inserted to and removed from the jack Hi1 of the input connector 356, and the pin Pi2 is inserted to and removed from the jack Hi2. Also, the pins Po10, Po11, Po20 and Po21 are provided on the end of the check cable 41 corresponding to the output connector 357. On the other end of the check cable 41, the pin Po10 is inserted to and removed from the jack Ho10 of the output connector 357, the pin Po11 is inserted to and removed from the jack Ho11 of the output connector 357, the pin Po20 is inserted to and removed from the jack Ho20 of the output connector 357, and the pin Po21 is inserted to and removed from the jack Ho21 of the output connector 357.

Each of the check cables 41 has arrangement positional information indicating the arrangement position on which the check cable 41 is fixed. In the check cable 41, each pin in the check cable 41 is electrically connected according to the arrangement positional information. For example, the pin Pi1 corresponds to the input pin of a first bit, and the pin Pi2 corresponds to the input pin of a second bit. The pin Po10 corresponds to a signal "0" of the first bit, the pin Po11 corresponds to a signal "1" of the first bit, the pin Po20 corresponds to the signal "0" of the second bit, and the pin Po21 corresponds to the signal "1" of the second bit. For example, when the arrangement positional information in the check cable 41 is "01", the pins Pi1 and Po10 are connected through a conductive wire L1, and the pins Pi2 and Po21 are connected through a conductive wire L2. Meanwhile, the jack Ho10 in the output connector 357 of the secondary station board 35P corresponds to the signal "0" of the first bit, the jack Ho11 corresponds to the signal "1" of the first bit, the jack Ho20 corresponds to the signal "0" of the second bit, and the jack Ho21 corresponds to the signal "1" of the second bit.

After arranging the secondary station board 35P on the set position, as indicated by an arrow, the pins Pi1 and Pi2 of the check cable 41 are inserted to the jacks Hi1 and Hi2 of the corresponding input connector 356, and the pins Po10 to Po21 are inserted to the jacks Ho10 to Ho21 of the output connector 357. In this case, current flows to the conductive wires L1 and L2 through the pins Pi1 and Pi2 inserted to the jacks Hi1 and Hi2. In addition, the current flows to the jack Ho10 through the pin Po10 connected to the pin Pi1 through the conductive wire L1, and the current flows to the jack Ho21 through the pin Po21 connected to the pin Pi2 through the conductive wire L2. Consequently, the secondary station board 35P may recognize that the arrangement positional information of the check cable 41 connected to the secondary station board 35P through the wire is "01". In this manner, the secondary station board 35P recognizes the arrangement positional information of the check cable 41 connected to the secondary station board 35P, aside from the positional information set in advance in each of the secondary station boards 35P. When the secondary station board 35P is arranged on a correct position, the positional information stored in the memory 352 and the arrangement positional information of the check cable 41 match. Meanwhile, the arrangement positional information of the check cable 41 recognized by the secondary station board 35P might be output to another secondary station 35, the primary station 34, and the main control unit 33, through a communication cable 37P connected to the secondary station board 35P.

Figure 4:
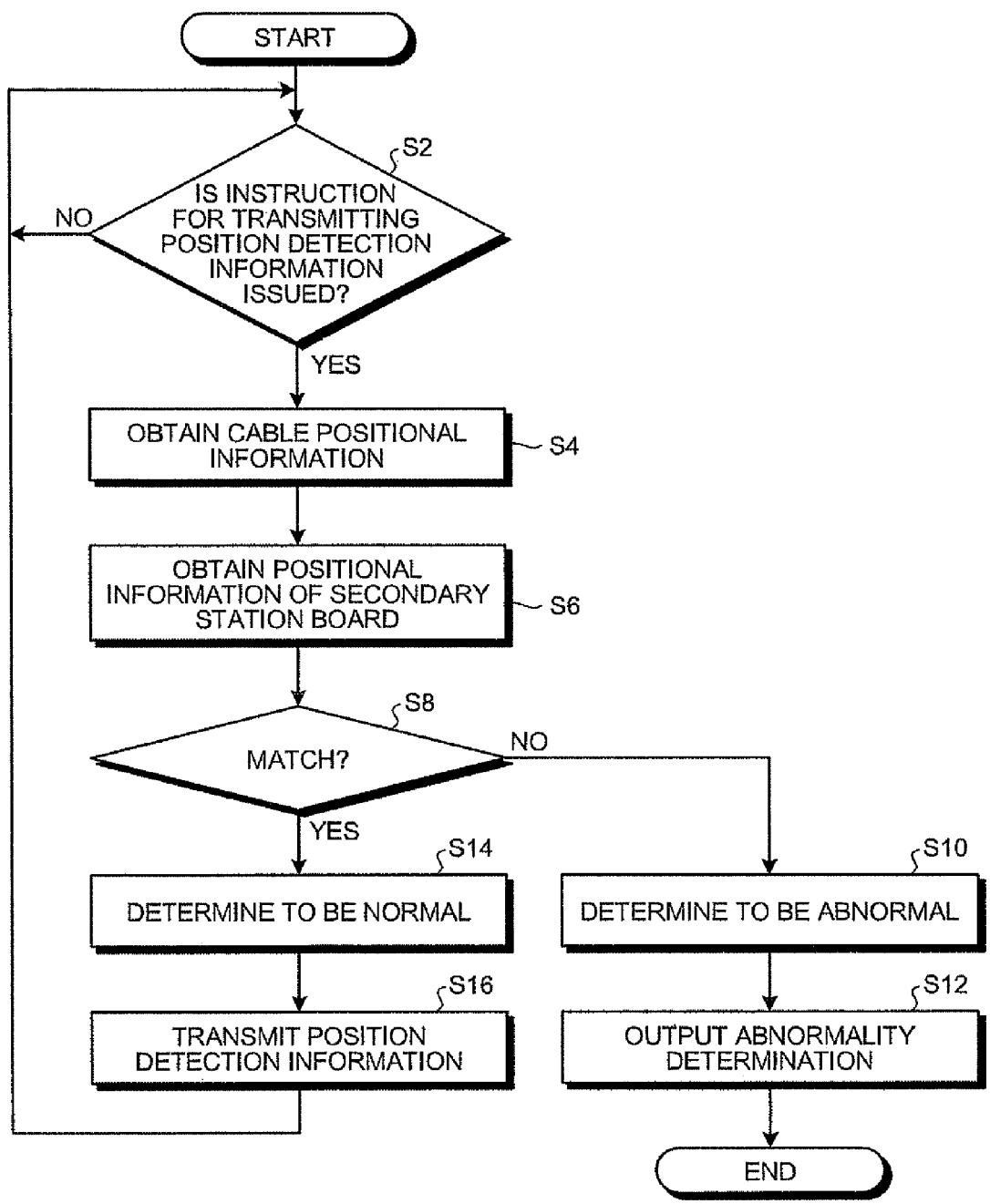
FIG. 4 is a flowchart showing a procedure to transmit position detection information detected by a sensor shown in FIG. 2.

Next, a procedure when transmitting the position detection information detected by a sensor 38 to which the secondary station 35 is connected to another secondary station 35 is described with reference to FIG. 4. As shown in FIG. 4, the secondary station 35 determines whether an instruction for transmitting position detection information is issued from the main control unit 33 to another secondary station (step S2). The secondary station 35 repeats a determination process at a step S2 until the instruction for transmitting position detection information is issued, and when the secondary station 35 determines that the instruction for transmitting position detection information is issued (step S2: Yes), the secondary station 35 obtains the arrangement positional information of the check cable 41 connected to the secondary station board 35P composing the secondary station 35 (step S4). Then, the secondary station 35 obtains the positional information set in advance in the secondary station 35 out of the information stored in the memory 352 (step S6). The secondary station 35 determines whether the arrangement positional information and the positional information match (step S8).

When the secondary station 35 determines that the arrangement positional information and the positional information do not match (step S8: No), the secondary station 35 determines that the secondary station board 35P composing the secondary station 35 is arranged on an incorrect position, and determines as abnormal (step S10). The secondary station 35 outputs this abnormality determination to the main control unit 33 through the primary station 34 (step S12). The main control unit 33 outputs the abnormality determination to the management device 4, and the management device 4 outputs a warning indicating that the arrangement position of the secondary station board 35P is incorrect and the position of the secondary station board 35P of which arrangement position is incorrect. An operator of the analyzer 1 checks the position of the secondary station board 35P arranged on the incorrect position by recognizing the warning, and may respond so as to arrange the secondary station board 35P again on the correct position.

On the other hand, when the secondary station 35 determines that the arrangement positional information and the positional information match (step S8: Yes), the secondary station 35 determines that the arrangement position of the secondary station board 35P composing the secondary station 35 is normal (step S14). Then, the secondary station 35 transmits the position detection information to another secondary station to which the transmission is instructed through the primary station 34 or directly (step S16), and after the position detection information is transmitted, the process proceeds to the step S2 to perform the determination process at the step S2. Meanwhile, when transmitting the position detection information from the secondary station 35 to the main control unit 33 also, the secondary station 35 transmits the position detection information by performing the procedure shown in FIG. 4.

In the analyzer 1 according to the first embodiment, the check cable 41 having the arrangement positional information is connected to each of the secondary station boards 35P composing each of the secondary stations 35 controlling each unit. The secondary station 35 transmits the information being the transmission object to outside after the arrangement positional information in the check cable 41 and the positional information set in the secondary station 35 match. Also, the secondary station 35 does not transmit the information being the transmission object and outputs the abnormality determination in which the secondary station board 35P is incorrectly arranged on a position different from the position on which this should be arranged, when the arrangement positional information in the check cable 41 and the positional information set in the secondary station 25 do not match.

In this manner, in the analyzer 1, the secondary station 35 transmits the information to outside after checking whether the secondary station board 35P composing the secondary station 35 is arranged on the correct position, so that the information transmitted from the secondary station board 35P is truly correct, and it becomes possible to transmit and receive the correct information between the secondary station 35 and the outside of the secondary station 35. Consequently, the analyzer 1 may prevent a communication failure due to an incorrect arrangement position of the secondary station board even when using a plurality of secondary station boards, which are difficult to be visually distinguished.

Figure 5:
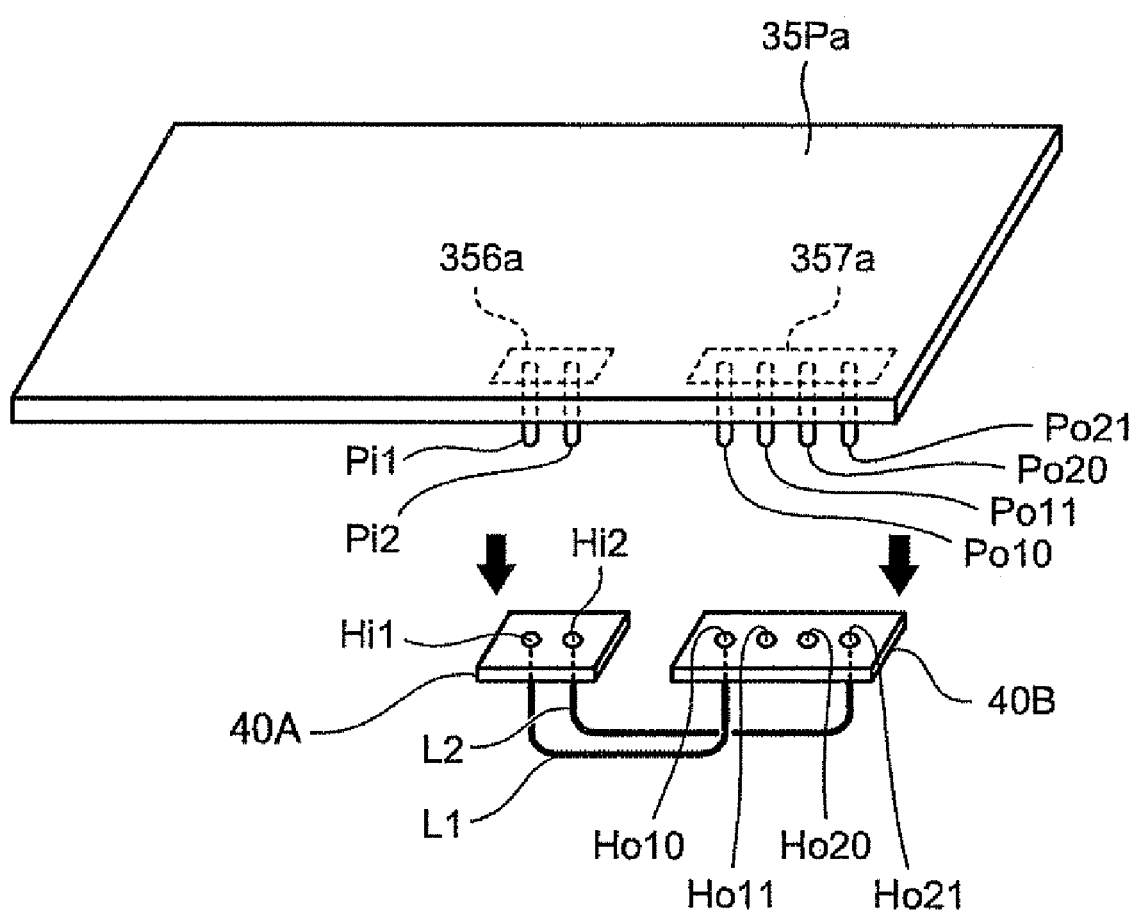
FIG. 5 is a view illustrating the arrangement of the secondary station substrate composing the secondary station shown in FIG. 2.

Meanwhile, about the analyzer 1, although the check cable 41 is described as a connecting unit of which arrangement position is fixed, it is not limited to this. For example, as shown in FIG. 5, the check connectors 40A and 40B of which arrangement positions are fixed may be used when using the secondary station board 35Pa provided with the input connector 356a and the output connector 357a each having the pin insertable to a predetermined jack.

The check connectors 40A and 40B are provided with the jack to and from which the pin of the input connector 356a and of the output connector 357a in the secondary station board 35Pa may be inserted and removed.

The jacks Hi1 and Hi2 are provided on the check connector 40A so as to correspond to the pins Pi1 and Pi2 of the input connector 356a in the secondary station board 35Pa. Also, the check connector 40B is provided with the jacks Ho10, Ho11, Ho20, and Ho21 so as to correspond to the pins Po10, Po11, Po20 and Po21 of the output connector 357a in the secondary station board 35Pa. In addition, in the check connectors 40A and 40B, the conductive wire L1 connects the jack Hi1 corresponding to the input jack of the first bit and the jack Ho10 corresponding to the signal "0" of the first bit, the conductive wire L2 connects the jack Hi2 corresponding to the input jack of the second bit and the jack Ho21 corresponding to the signal "1" of the second bit, and the jack Ho11 corresponding to the signal "1" of the first bit and the jack Ho20 corresponding to the signal "0" of the second bit are not connected to the jacks Hi1 and Hi2 of the check connector 40A. Also, as indicated by an arrow, each pin of the secondary station board 35Pa is inserted to each jack of the check connectors 40A and 40B and current flows through the conductive wires L1 and L2, and as a result, the secondary station board 35Pa may recognize that the arrangement positional information of the check connectors 40A and 40B connected to the secondary station board 35Pa is "01". Meanwhile, in the check cable 41 and the check connectors 40A and 40B, a bit number of the arrangement positional information of the check cable 41 and the check connectors 40A and 40B may be increased by increasing the number of jacks, pins, and conductive wires connecting the jack or the pin corresponding to the arrangement positional information. In the secondary station boards 35P and 35Pa, the jack or the pin may be provided so as to correspond to the number of jacks and pins of the check cable 41 and the check connectors 40A and 40B.

Also, a plurality of network lines may be provided to connect the main control unit 33 and each secondary station 35.

Figure 6:
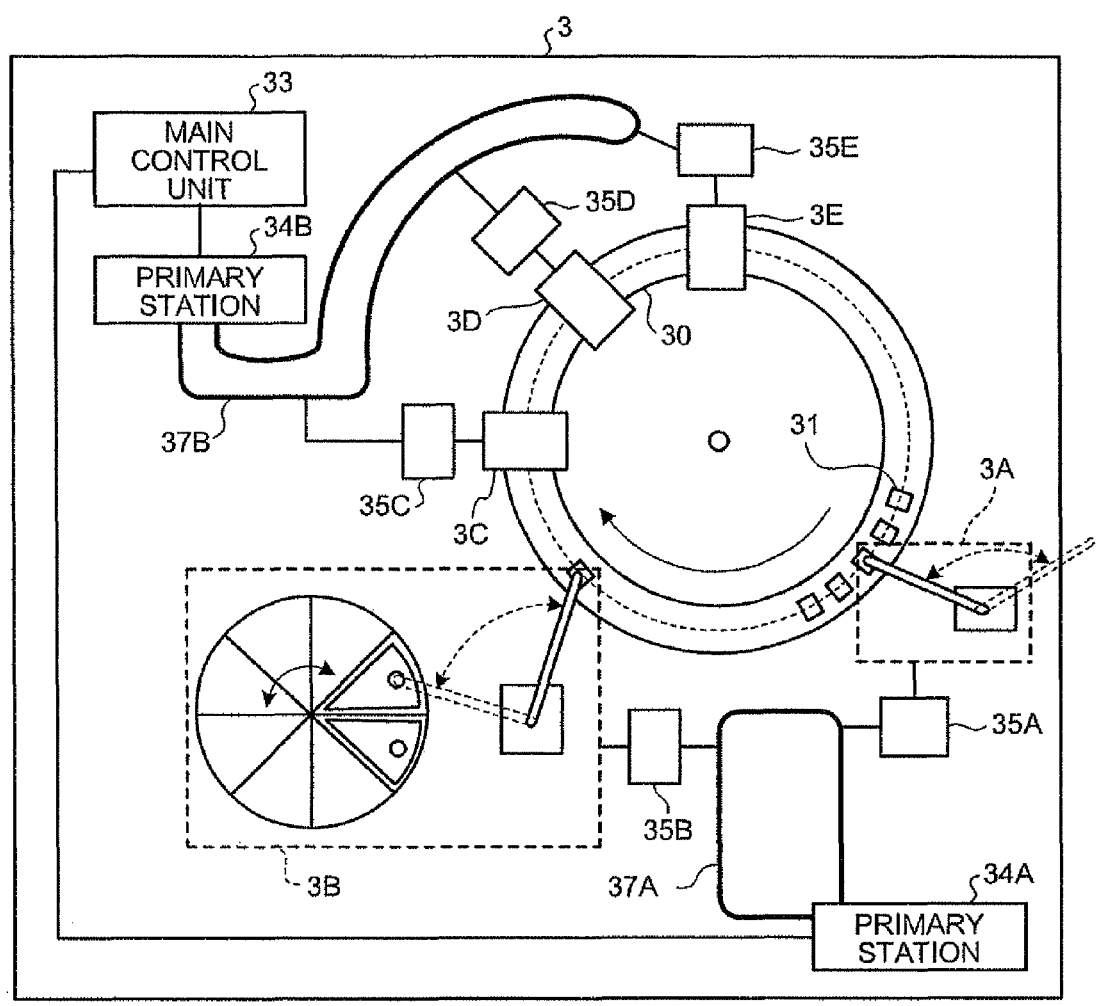
FIG. 6 is a view illustrating a connection state of each component composing the analyzer shown in FIG. 1.

For example, as shown in FIG. 6, a plurality of networks 37 may be provided so as to correspond to the arrangement positions of the secondary stations 35. In this case, a network line 37A connected to the secondary station 35A connected to an adjacent specimen dispensing unit 3A and to the secondary station 35 connected to the reagent dispensing unit 3B, and a network line 37B connected to the secondary station 35C connected to an adjacent stirring unit 3C, the secondary station 35D connected to the light measuring unit 3D, and the secondary station 35E connected to the cleaning unit 3E are provided to connect the main control unit 33 and each secondary station 35. Consequently, complicated wiring composing the network or the like may be prevented. Meanwhile, a primary station 34A connected to the network line 37A and a primary station 34B connected to the network line 37B are provided between each of the network lines 37A and 37B and the main control unit 33, and the instruction is smoothly output from the main control unit 33 to each of the secondary stations 35. Also, in the analyzer 1, a plurality of network lines may be provided so as to correspond to the function of each unit to which the secondary station 35 is connected. For example, the analyzer 1 provides a plurality of network lines for the secondary station connected to the unit operating even in a time period in which the analysis process is not performed and for another secondary station. Also, the analyzer 1 may provide a plurality of network lines so as to correspond to both of the arrangement position of the secondary station 35 and the function of each system to which the secondary station 35 is connected.

Figure 7:
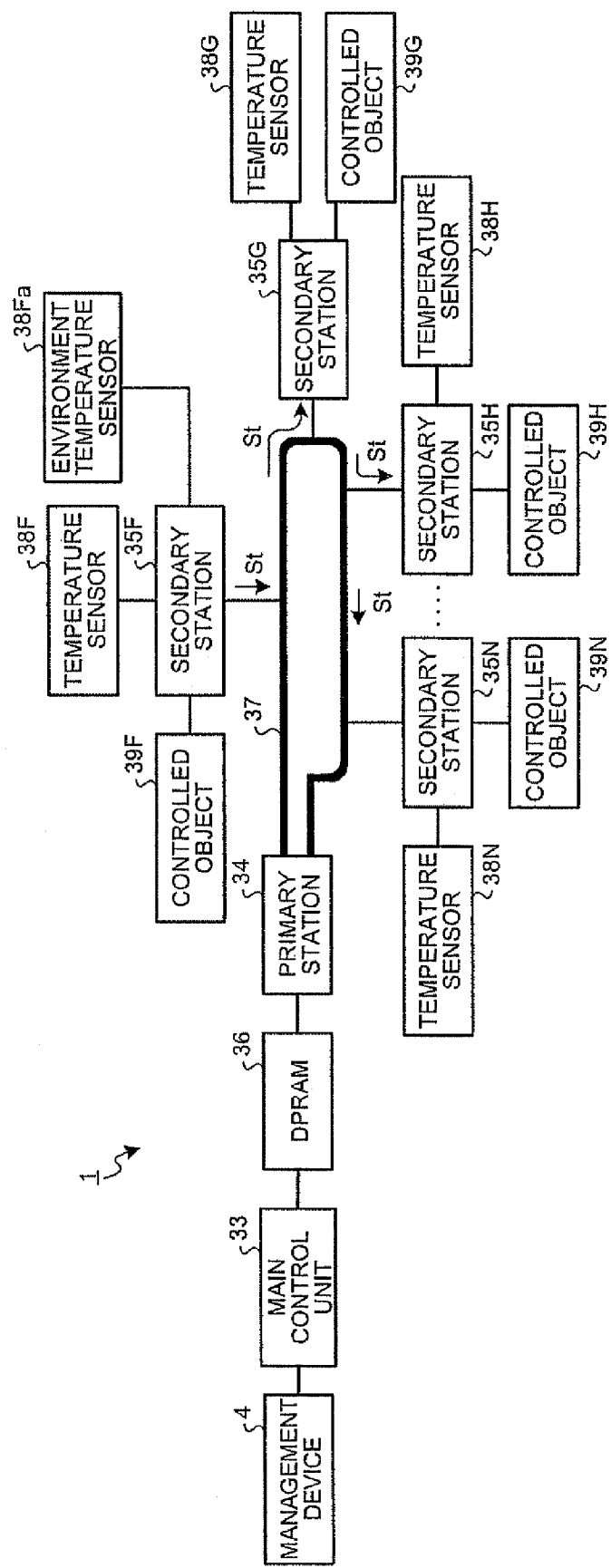
FIG. 7 is a block diagram showing a configuration of the analyzer according to a second embodiment.

Next, a second embodiment is described. In the second embodiment, a case in which the secondary station 35 is connected to the sensor for detecting a temperature is described. FIG. 7 is a view illustrating a connection status of each component of the analyzer 1 in the second embodiment.

As shown in FIG. 7, a secondary station 35F is connected to a controlled object 39F such as each unit and a heater provided in the vicinity of each unit, a temperature sensor 38F for detecting the temperature of the controlled object 39F, and an environment temperature sensor 38Fa for detecting a temperature of an ambient environment of the secondary station 35F to control the temperature sensor 38F, the environment temperature sensor 38Fa, and the controlled object 39F. Other secondary stations 35G to 35N are connected to controlled objects 39G to 39N and temperature sensors 38G to 38N for detecting temperature of the controlled objects 39G to 39N, respectively, to control each of the temperature sensors 38G to 38N and each of the controlled objects 39G to 39N. Meanwhile, the environment temperature sensor 38Fa is provided only to the secondary station 35F. The secondary stations 35F to 35N communicate with another one of the secondary stations 35F to 35N through the network 37.

The secondary station 35F changes a target temperature of the controlled object 39F according to the temperature of the ambient environment detected by the environment temperature sensor 38Fa, which is connected, to control the temperature of the controlled object 39F. Also, the secondary station 35F transmits a signal St corresponding to the temperature of the ambient environment detected by the environment temperature sensor 38Fa. Meanwhile, as in the first embodiment, the secondary station 35F may directly transmit the signal St to another one of the secondary stations 35G to 35N being the destination, and may transmit the signal St through the primary station 34. Specifically, the secondary station 35F transmits the information specifying any one of the second stations 35G to 35N being the destination to the primary station 34 together with the signal St, and according to received information, the primary station 34 specifies any one of the secondary stations 35G to 35N being the destinations to transmit the signal St. The secondary stations 35G to 35N receive the signal St transmitted from the secondary station 35F, changes the target temperature of each of the controlled objects 39G to 39N according to the temperature of the ambient environment detected by the environment temperature sensor 38Fa, and controls the temperature of the controlled objects 39G to 39N, respectively. Also, as in the first embodiment, each of the secondary stations 35F to 35N is arranged on the predetermined arrangement position, and thereafter, connected to the check cable 41 shown in FIG. 3.

Figure 8:
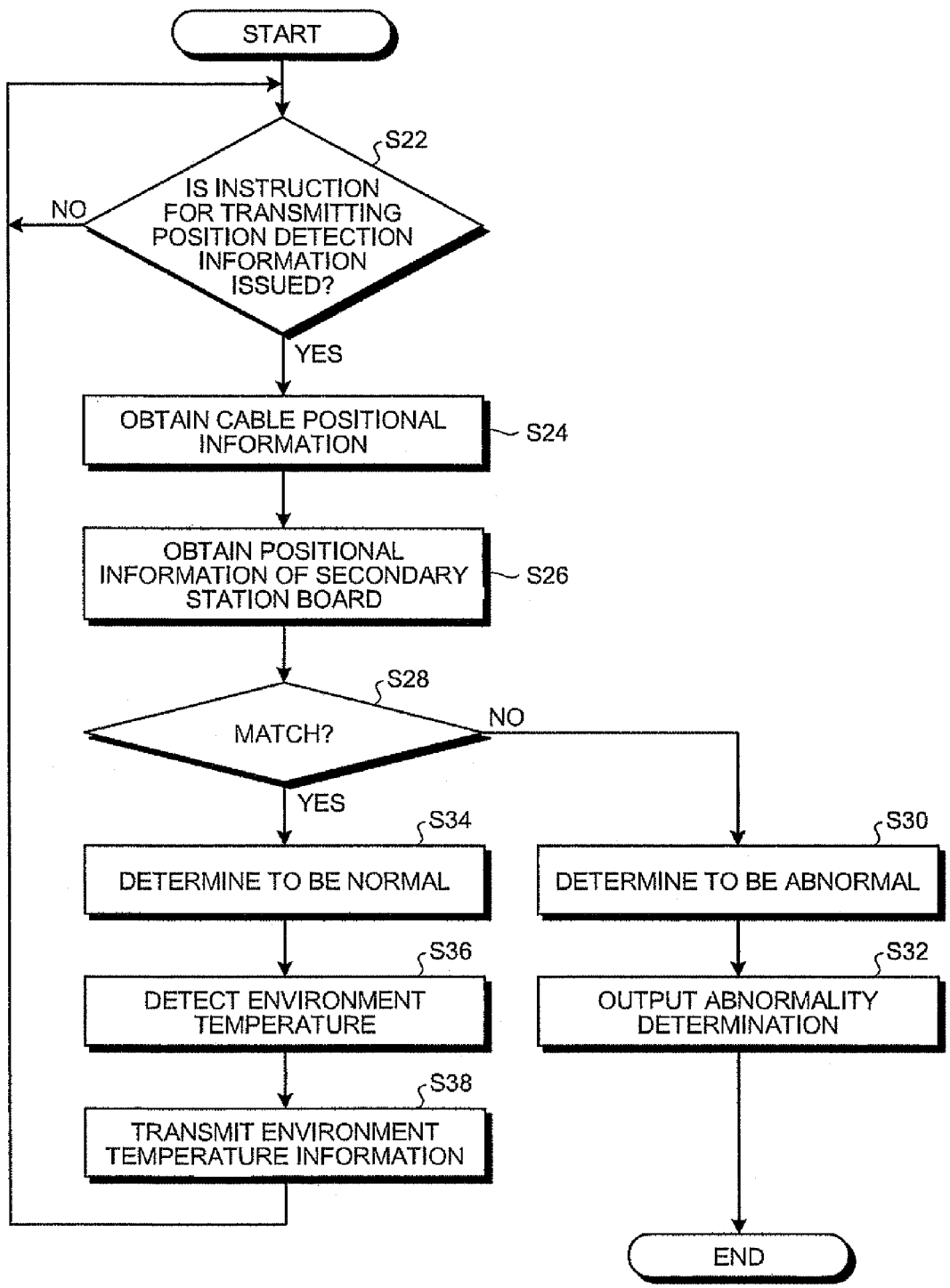
FIG. 8 is a flowchart showing a procedure to transmit a detected temperature by an environment temperature sensor shown in FIG. 7.

Next, a procedure when the secondary station 35F transmits the temperature of the ambient environment detected by the environment temperature sensor 38Fa to another secondary station 35 is described with reference to FIG. 8. As shown in FIG. 8, the secondary station 35F determines whether the instruction for transmitting environment temperature is issued from the main control unit 33 to another secondary station through the primary station 34 (step S22). The secondary station 35F repeats the determination process at the step S22 until the instruction for transmitting environment temperature is issued, and when it is determined that the instruction for transmitting environment temperature is issued (step S22: Yes), the secondary station 35F obtains the arrangement positional information of the check cable 41 connected to the secondary station 35F (step S24). Then, the secondary station 35F obtains the positional information set in advance in the secondary station 35F out of the information stored in the memory 352 in the secondary station board 35P composing the secondary station 35F (step S26). The secondary station 35F determines whether the obtained arrangement positional information and the positional information match (step S28).

When the secondary station 35F determines that the arrangement positional information and the positional information do not match (step S28: No), the secondary station 35F determines that the secondary station board 35P composing the secondary station 35F is arranged incorrectly, and determines as abnormal (step S30). The secondary station 35F outputs the abnormality determination to the main control unit 33 through the primary station 34 (step S32). The main control unit 33 outputs the abnormality determination to the management device 4, and the management device 4 outputs the warning indicating that the arrangement position of the secondary station board 35P is incorrect and the position of the secondary station board 35P of which arrangement position is incorrect.

On the other hand, when the secondary station 35F determines that the arrangement positional information and the positional information match (step S28: Yes), the secondary station 35F determines that the arrangement position of the secondary station board 35P composing the secondary station 35F is normal (step S34). Then, the secondary station 35F allows the environment temperature sensor 38Fa to detect the temperature of the ambient environment (step S36). Then the secondary station 35F transmits the environment temperature information regarding the temperature of the ambient environment detected by the environment temperature sensor 38Fa to another secondary station to which the transmission is instructed, through the primary station 34 or directly (step S38), and the process proceeds to the step S22 to perform the determination process at the step S22.

Figure 9:
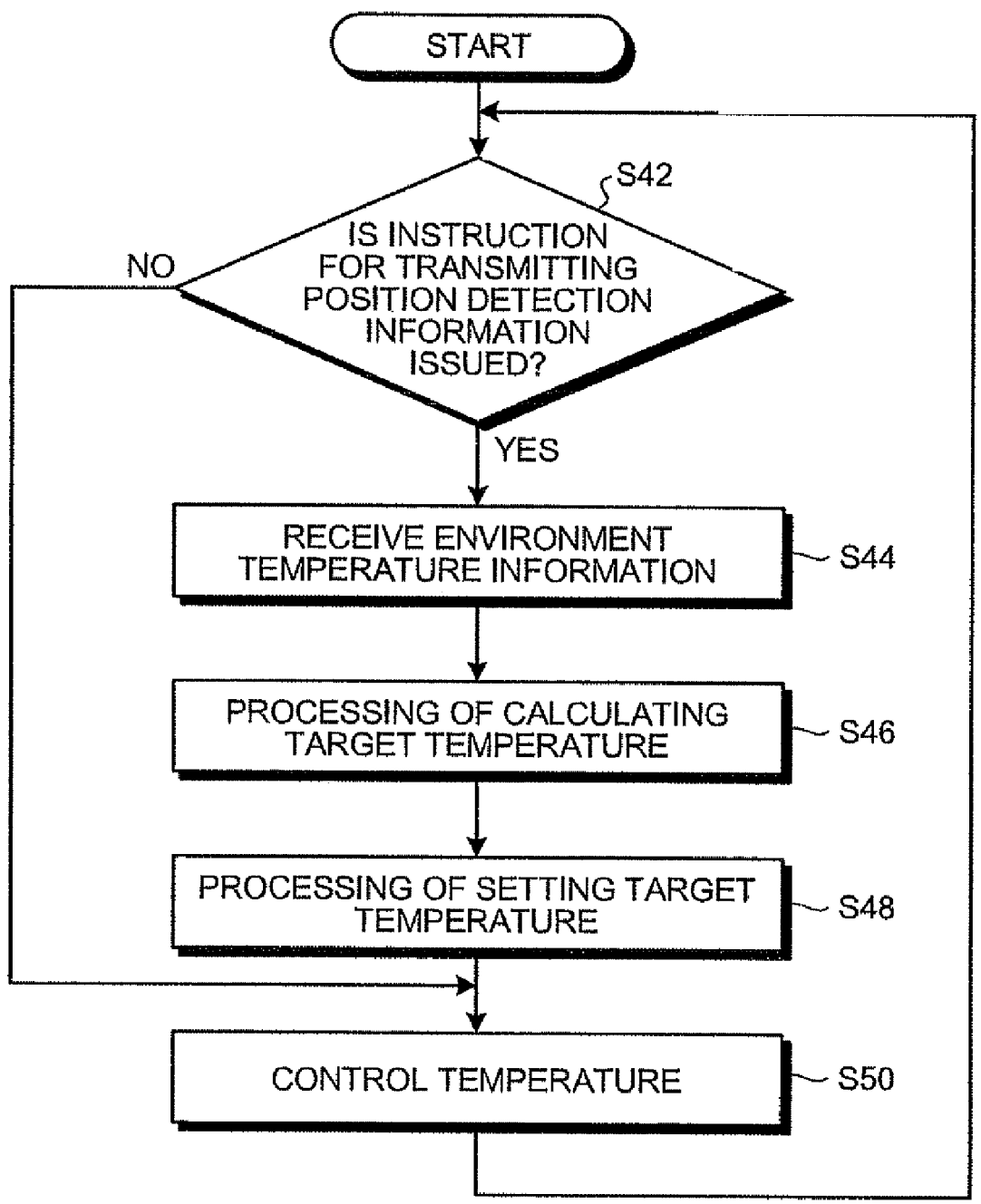
FIG. 9 is a flowchart showing a procedure to set a target temperature in the secondary station shown in FIG. 7.

Next, a procedure when the secondary stations 35G to 35N, which are not connected to the environment temperature sensor 38Fa, set the target temperature of the controlled objects 39G to 39N, respectively, is described with reference to FIG. 9. As shown in FIG. 9, the secondary stations 35G to 35N determine whether the instruction for changing the target preset temperature of the controlled objects 39G to 39N is issued, respectively, from the main control unit 33 (step S42). When each of the secondary stations 35G to 35N determines that instruction for changing the target preset temperature is not issued(step S42: No), the process proceeds to a step S50 to control the temperature of the controlled objects 39G to 39N according to the set target temperature. On the other hand, when the secondary stations 35G to 35N determine that the instruction for changing the target preset temperature is issued(step S42: Yes), the secondary stations 35G to 35N receive the environment temperature information transmitted from the secondary station 35F (step S44).

Then, each of the secondary stations 35G to 35N perform a target temperature calculation process for calculating the target temperature of the controlled objects 39G to 39N, respectively, using the temperature of the ambient environment in the received environment temperature information (step S46).

Specifically, each of the secondary stations 35G to 35N calculates a target temperature T using the following equation (1):

$$T=a\times t+b \qquad (1).$$

In the equation (1), coefficients a and b are set in advance for each of the secondary stations 35G to 35N, and t represents the temperature of the ambient environment detected by the environment temperature sensor 38Fa in the environment temperature information. For example, in the secondary station 35G, a value of 1.2 is set as the coefficient a, and a value of (−1) is set as the coefficient b. When the temperature of the ambient environment is 37.0° C. according to the received environment temperature information, the secondary station 35G calculates the target temperature T of the controlled object 39G as 43.4° C. by using the equation (1). Meanwhile, the secondary station 35F likewise calculates the target temperature of the controlled object 39F using the detected temperature of the environment temperature sensor 38Fa to which the secondary station 35F is connected and the equation (1).

Then, each of the secondary stations 35G to 35N performs a target temperature set process (step S48) for changing and setting the target temperature of each of the controlled objects 39G to 39N to the temperature calculated in the target temperature calculation process (step S46), and controls the temperature of each of 39G to 39N so as to be the set target temperature (step S50).

In this manner, in the second embodiment, the secondary station 35F transmits the environment temperature information to the outside of the secondary station 35 after checking whether the secondary station board 35P composing the secondary station 35F is arranged on the correct position. Therefore, the environment temperature information transmitted from the secondary station 35F is truly correct, and even when using a plurality of secondary station boards, which are difficult to be visually distinguished from each other, the communication failure due to the incorrect arrangement position of the secondary station board may be prevented, and it becomes possible to transmit and receive the correct environment temperature information between the secondary station 35F and another one of the secondary stations 35G to 35N.

Conventionally, the target temperature of the controlled object is set by setting the environment temperature sensor for each secondary station, so that this requires a complex system configuration. On the other hand, in the second embodiment, the secondary stations 35G to 35N may obtain the temperature of the ambient environment detected by the environment temperature sensor 38Fa connected to the secondary station 35F through the network 37. Therefore, according to the second embodiment, it is not required to provide the environment temperature sensor for each of the secondary stations 35G to 35N, and a simple system configuration may be realized. Also, conventionally, there is variation in the detected temperature among the environment temperature sensors provided for each secondary station, so that it is not possible to control the temperature with high accuracy with respect to the controlled object connected to each of the secondary station due to the variation in the detected temperature. On the other hand, according to the second embodiment, it is not required to provide the environment temperature sensor for each of the secondary stations 35G to 35N, so that the temperature may be controlled with high accuracy without being affected by the variation in the detected temperature among the environment temperature sensors.

Meanwhile, in the first and second embodiments, although a case in which the secondary station 35 transmits the information detected by the sensor connected to the secondary station 35 to another secondary station 35 is described, it is not limited to this, and the information stored in the secondary station 35 may be transmitted to another secondary station 35.

Also, in the first and second embodiments, although a case in which the secondary station 35, which has received the information transmission instruction, transmits the information to outside after checking whether the secondary station board 35P composing the secondary station 35 is arranged on the correct position is described, it is not limited to this. For example, in a case in which the secondary station 35 instructs another secondary station to transmit the information also, the transmission of the information may be allowed to the secondary station 35, which instructs the transmission, when it is determined that the positional information in the secondary station, which instructs the transmission, and the arrangement positional information of the check cable 41 connected to the secondary station board 35P composing the secondary station 35 match. In this manner, the secondary station 35 may communicate with the communication object when the secondary station 35 determines that the positional information in the secondary station 35 and the arrangement positional information by the check cable 41 connected to the secondary station board 35P composing the secondary station 35 match, and may communicate with a secondary control unit being the communication object when the secondary station 35 determines that the positional information of the secondary station 35 being the communication object and the arrangement positional information by the check cable 41 connecting to the secondary station board 35P composing the secondary station 35 being the communication object match.

Next, a third embodiment is described. In the third embodiment, a program update process stored in the secondary station by the main control unit is described. Meanwhile, the analyzer according to the third embodiment has the similar configuration as the analyzer according to the first and second embodiments.

Figure 10:
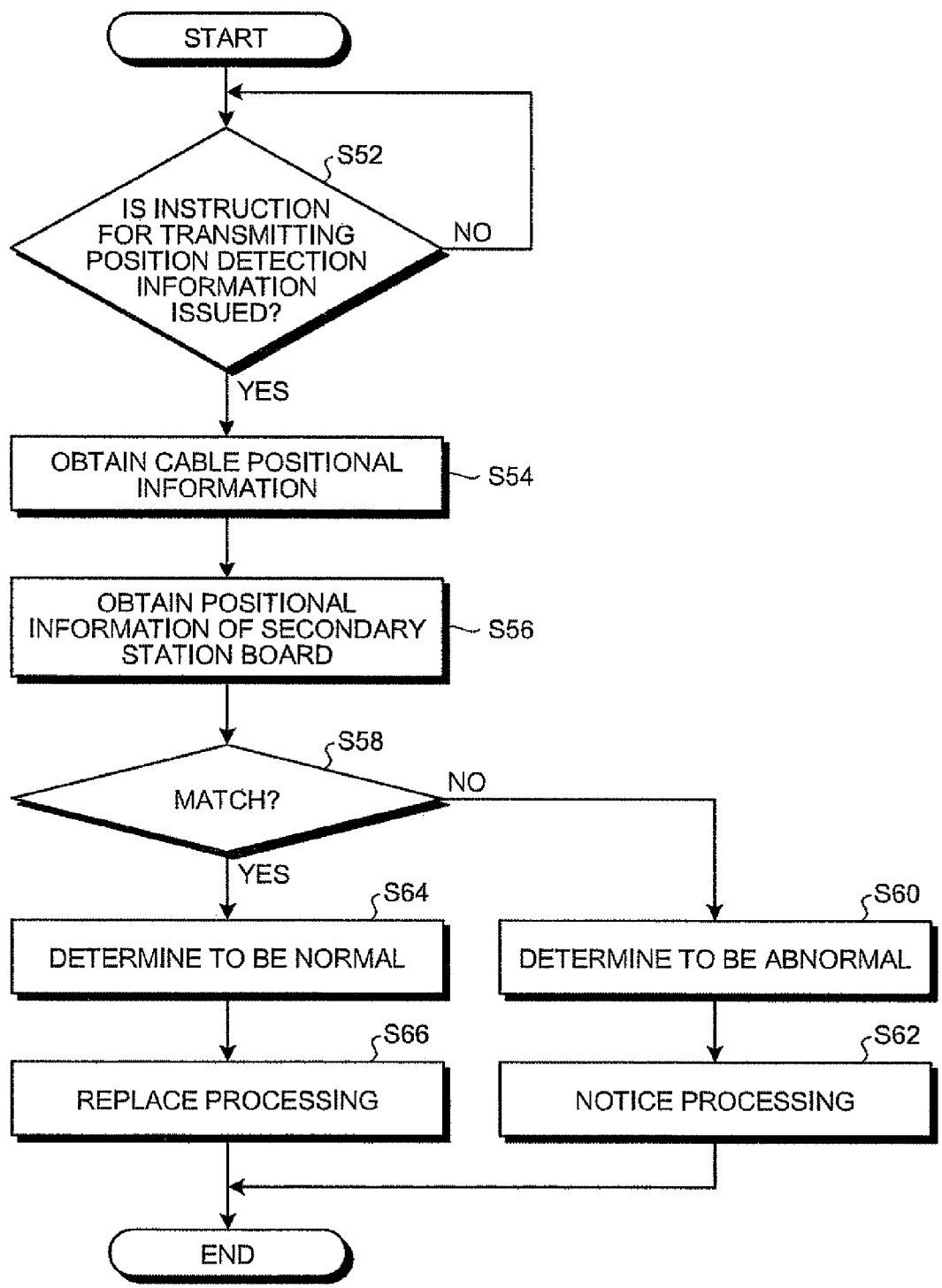
FIG. 10 is a flowchart showing a procedure to update a program stored in the secondary station in a third embodiment.

FIG. 10 is a flowchart showing a procedure of the program update process stored in the secondary station 35 in the third embodiment. As shown in FIG. 10, first, the main control unit 33 determines whether a rewrite instruction of the program stored in a predetermined secondary station 35 from the management device 4 is issued (step S52). The main control unit 33 repeats the determination process at the step S52 until the rewrite instruction of the program is issued, and when the main control unit 33 determines that the rewrite instruction is issued (step S52: Yes), the main control unit 33 obtains the arrangement positional information of the check cable 41 connected to the secondary station board 35P composing the secondary station 35 from the secondary station 35 instructed to rewrite the program through the primary station 34 and the network 37 (step S54). Then, the main control unit 33 obtains the positional information set in advance in the secondary station 35, which is instructed to rewrite the program (step S56). The main control unit 33 determines whether the obtained arrangement positional information and the positional information match (step S58).

When the main control unit 33 determines that the arrangement positional information and the positional information do not match (step S58: No), this determines that the secondary station board 35P composing the secondary station 35 is arranged incorrectly and determines as abnormal (step S60). The main control unit 33 outputs the abnormality determination to the management device 4, and the management device 4 outputs the warning indicating that the arrangement position of the secondary station board 35P, which is the rewriting object of the program, is incorrect, and the position of the secondary station board 35P of which arrangement position is incorrect (step S62).

On the other hand, when the main control unit 33 determines that the arrangement positional information and the positional information match (step S58: Yes), the main control unit 33 determines that the arrangement position of the secondary station board 35P composing the secondary station 35 is normal (step S64). Then, the main control unit 33 instructs the secondary station 35, which is instructed to rewire the program, to rewrite the program, through the primary station 34 and the network 37, and the secondary station 35 receiving the program rewrite instruction performs the rewrite process for rewriting the program stored in the memory according to the received rewrite instruction (step S66).

Conventionally, there is a problem that the program is incorrectly rewritten on the control board different from the control board, which is the rewrite target, as a result of incorrectly arranging the secondary station board having the similar hardware configuration on the position different from the position on which this should be arranged.

On the other hand, in the third embodiment, the program is rewritten after checking whether the secondary station board 35P composing the secondary station 35 being the rewrite target of the program is arranged on the correct position. Also, in the third embodiment, when the secondary station board 35P having the similar hardware configuration is incorrectly arranged on the position different from the position on which this should be arranged, the predetermined warning is output. Therefore, according to the third embodiment, even when using a plurality of secondary station boards which is difficult to be visually distinguished from each other, the communication failure due to the incorrect arrangement position of the secondary station board may be prevented, and the program may be correctly rewritten without mistaking the secondary station board 35P being the rewriting object. Also, in the third embodiment, the program in the secondary station 35 is rewritten through the network 37. Therefore, according to the third embodiment, removing of the secondary station board 35P and readjustment of the arrangement position of the secondary station board 35P due to the removing of the secondary station board 35P, which are conventionally required, are not necessary, and the program stored in the secondary station board 35P may be rapidly and simply rewritten.

Meanwhile, the main control unit 33 may rewrite the information including the program and write the information, after performing the steps S54 to S64 shown in FIG. 10. Also, the main control unit 33 may communicate with the secondary station 35 being the communication object after performing the steps S54 to S64 shown in FIG. 10 to the secondary station 35 being the communication object. Also, the main control unit 33 may instruct the predetermined secondary station to transmit the information to another secondary station after performing the steps S54 to S64 shown in FIG. 10. Consequently, the main control unit 33 may correctly control each secondary station 35.

Figure 11:
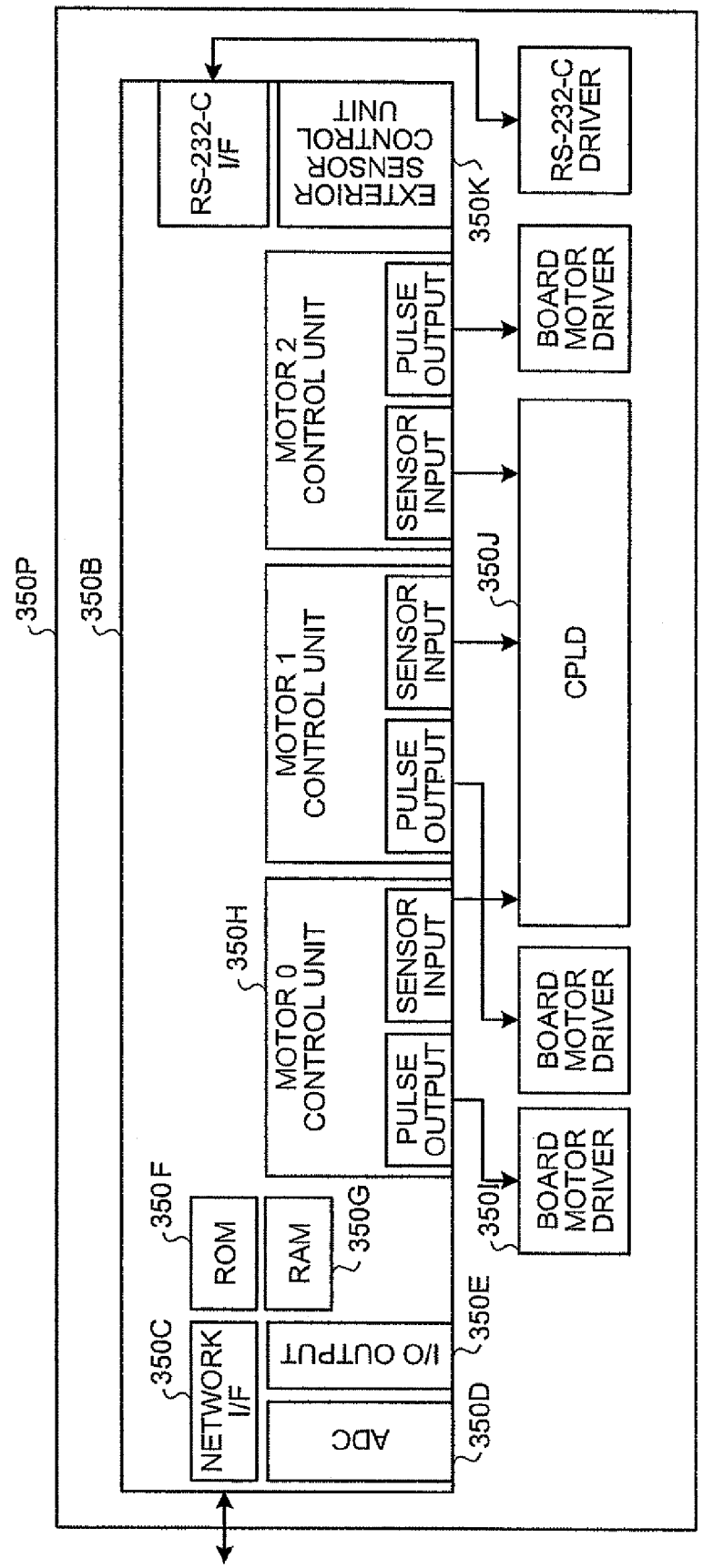
FIG. 11 is a view illustrating a configuration of the secondary station substrate shown in FIG. 3.

Also, the secondary station board 35P is composed of a secondary station board 350P shown in FIG. 11, for example. The secondary station board 350P has a one-chip microcomputer 350B. The one-chip microcomputer 350B has a board motor driver 350I and a CPLD 350J, and has a network interface 350C, an AD converter 350D, an I/O output unit 350E, an ROM 350F, an RAM 350G, each motor control unit 350H controlling the board motor driver 350I and the CPLD 350J, and an exterior sensor control unit 350K for controlling each exterior sensor connected to the secondary station board 350P. The one-chip microcomputer 350B has a function of controlling an actuator principally involving a pulse motor control, collecting sensor information, and a network interface. The one-chip microcomputer 350B optionally selects a sensor out of a plurality of sensors in relation to an operation of the actuator to allow the sensor to operate. Also, it is possible to feed back a Busy signal indicating that the sensor or the motor is active in another unit connected to the network 37 to the operation of the actuator controlled by the secondary station board 350P. The program, which operates on the one-chip microcomputer 350B and is stored in the CPLD 350J may be downloaded from the main control unit 33 through the network 37 and may be rewritten.

Also, the analyzer, the communication method and the communication program in the analyzer described in the above-described first to third embodiments may be realized by executing the program prepared in advance by the management device 4, which is a computer system such as a personal computer and a work station, and by the main control units 23 and 33 controlled by the management device 4. Hereinafter, the computer system for executing the program having the function similar to that of the analyzer described in the above-described first to third embodiments is described.

Figure 12:
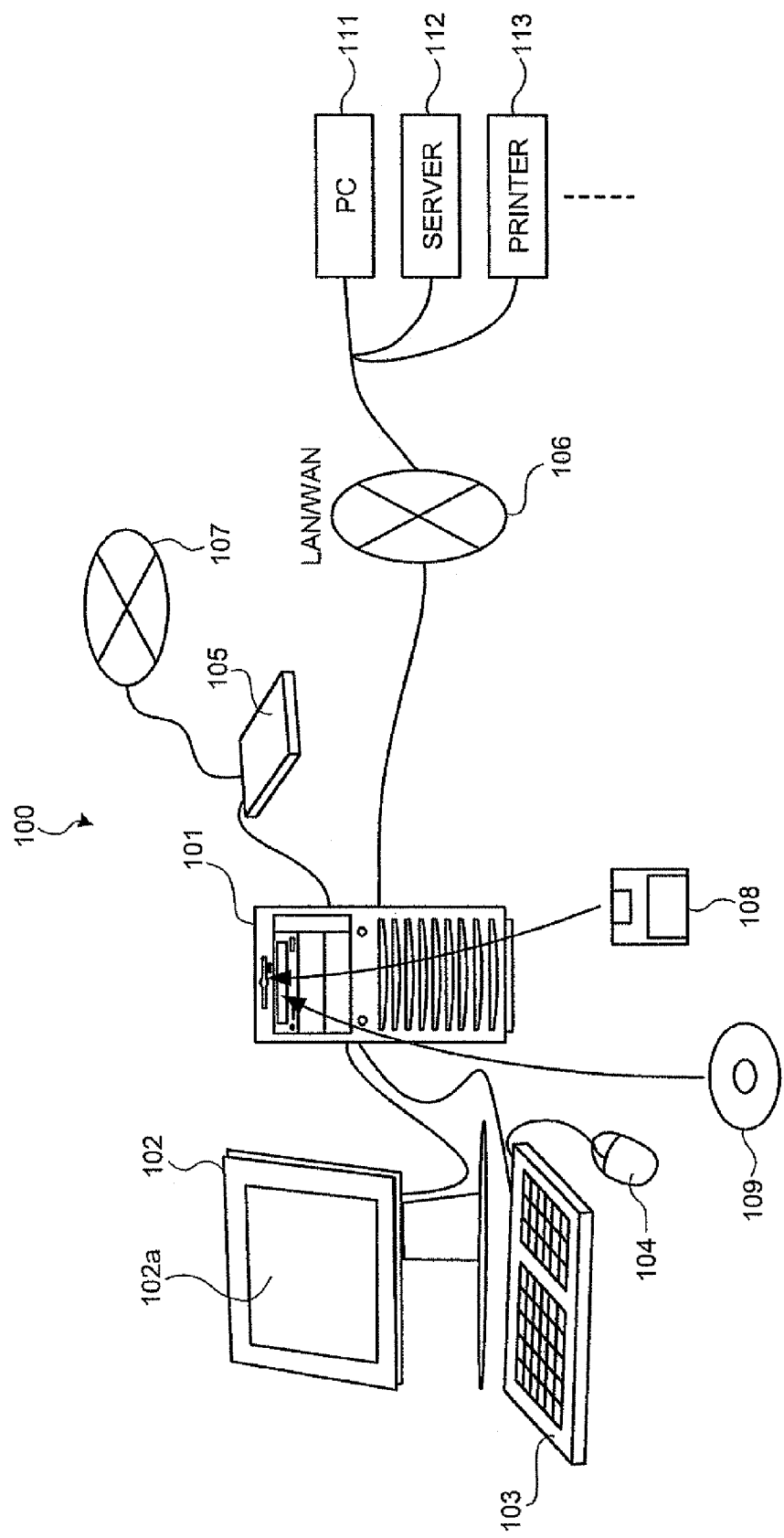
FIG. 12 is a configuration diagram showing a configuration of a computer system using the first to third embodiments.
Figure 13:
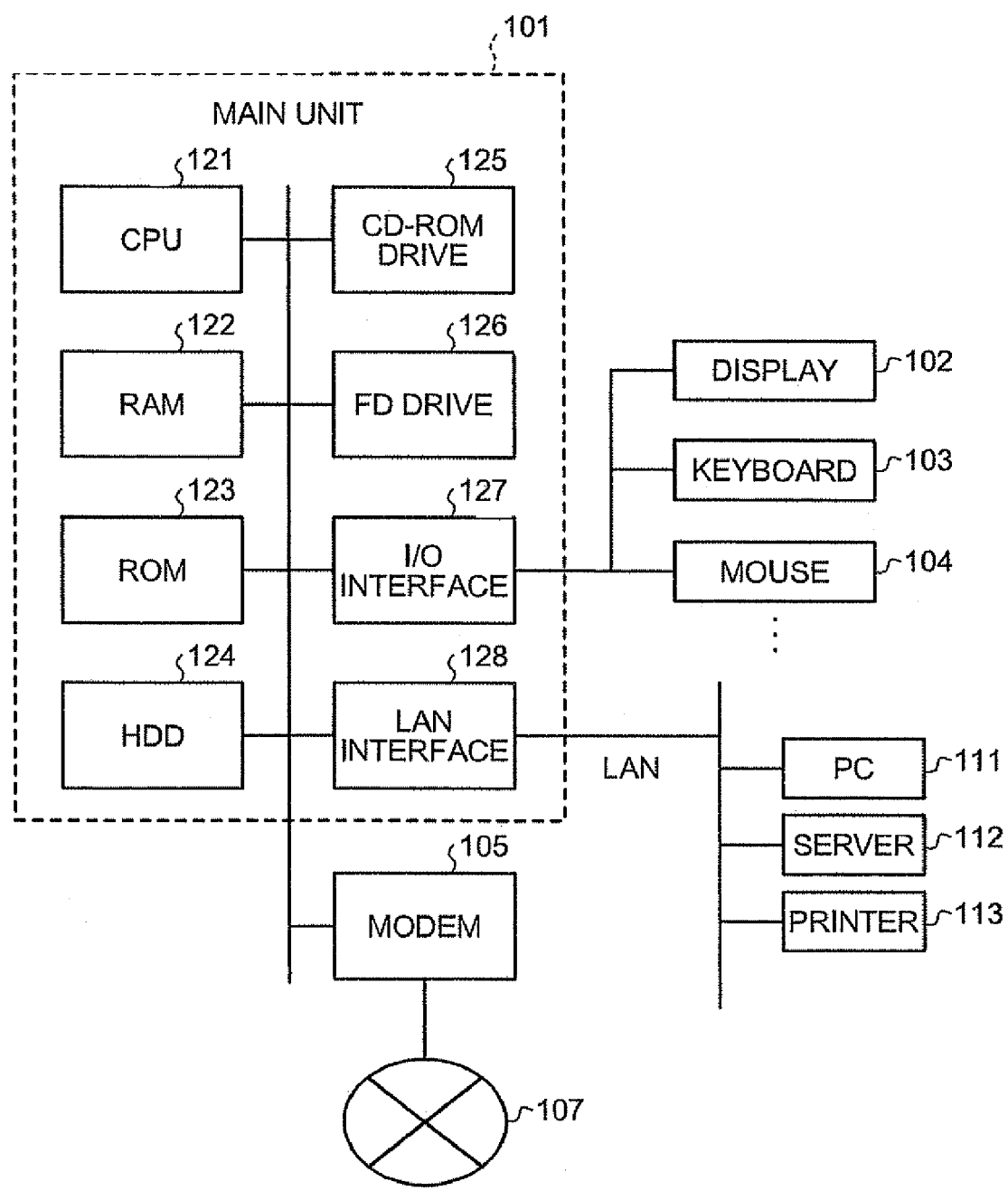
FIG. 13 is a block diagram showing a configuration of a main unit of the computer system shown in FIG. 12.

FIG. 12 is a system configuration diagram showing a configuration of the computer system using the above-described embodiments, and FIG. 13 is a block diagram showing a configuration of a main part of the computer system. As shown in FIG. 12, a computer system 100 according to this embodiment is provided with a main part 101, a display 102 for displaying information such as an image on a display screen 102a by the instruction from the main unit 101, a keyboard 103 for inputting various pieces of information to the computer system 100, and a mouse 104 for specifying an optional position on the display screen 102a of the display 102.

Also, the main unit 101 in the computer system 100 is provided with a CPU 121, a RAM 122, a ROM 123, a hard disk drive (HDD) 124, a CD-ROM drive 125 for receiving a CD-ROM 109, a FD drive 126 for receiving a flexible disk (FD) 108, an I/O interface 127 for connecting the display 102, the keyboard 103 and the mouse 104, and a LAN interface 128 for connecting to a local area network or a wide area network (LAN/WAN) 106, as shown in FIG. 13.

Further, to the computer system 100, a modem 105 for connecting to a public line 107 such as the Internet is connected, and another computer system (PC) 111, a server 112, and a printer 113 are connected through the LAN interface 128 and the LAN/WAN 106.

The computer system 100 realizes the analyzer by reading the program stored in a predetermined memory media and executing the same. Herein, the predetermined memory media includes any of the memory media recording the program readable by the computer system 100, such as "fixed physical media" such as the hard disk drive (HDD) 124, the RAM 122 and the ROM 123, provided inside and outside of the computer system 100 in addition to "portable physical media" such as the flexible disk (FD) 108, the CR-ROM 109, an MO disk, a DVD disk, a magneto optical disk, and an IC card, further "communication media" holding the program on a short-time basis when transmitting the program such as the public line connected through the modem 105 and the LAN/WAN 106 to which another computer system 111 and the server 112 are connected.

That is to say, the program is recorded so as to be readable by the computer to the memory media such as the above-described "portable physical media", "fixed physical media", and "communication media", and the computer system 100 realizes the communication method in this analyzer by reading the program from such memory media and executing the same. Meanwhile, the program is not limited to be executed by the computer system 100, and the present invention is also applicable in a case in which another computer system 111 and the server 112 executes the program and in a case in which they cooperate with each other to execute the program.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An analyzer system comprising:
   an analyzer for analyzing a specimen comprising a measuring system for measuring the specimen, the measuring system includes a plurality of processing units; and
   a controlling system for controlling operations of the measuring system, the controlling system comprising:
      a main control unit configured to instruct each of the processing units of the measuring system of a process operation;
      a primary station configured to that time-divisionally output an instruction by the main control unit;
      a plurality of secondary station boards each connected to a corresponding processing unit, each of the secondary station boards configured to control an operation of the corresponding processing unit according to the instruction by the main control unit, each of the secondary station boards including memory for storing positional information set in advance, and each of the secondary station boards comprising an input check connector and an output check connector;
      a network configured to connect the primary station and the secondary station boards; and
      a plurality of check cables that are arranged at fixed positions configured to connect between the input check connector and the output check connector of corresponding secondary station boards, each of the check cables includes inside an arrangement of conductive wires configured such that each of the check cables matches with a corresponding secondary station board according to the fixed position of the respective check cable;
   wherein the processing units connected to each of the secondary station boards are configured to generate a signal conducted from the input check connector to the corresponding output check connector that represents arrangement positional information indicating the fixed position of the matching check cable connected to the respective secondary station board, and the processing units further configured to compare the positional information stored in the respective secondary station board with the arrangement positional information represented by the signal to determine whether the respective secondary station board is located at the correct position in the system.

2. The analyzer system according to claim 1, wherein each of the plurality of secondary station boards communicates normally when the processing units determine that the positional information obtained and the arrangement positional information matches.

3. The analyzer system according to claim 1, wherein each of the plurality of secondary station boards further comprises a sensor configured to detect a position of a detection object, wherein each of the plurality of secondary station boards is further configured to transmit information regarding the position of the detection object detected by the sensor to another of the plurality of secondary station boards through the primary station, or configured to directly transmit to another of the plurality of secondary station boards.

4. The analyzer system according to claim 1, comprising: wherein each of the plurality of secondary station boards further comprises a temperature sensor configured to detect a temperature, wherein each of the plurality of secondary station boards is further configured to transmit information regarding the temperature detected by the temperature sensor to another of the plurality of secondary station boards through the primary station, or configured to directly transmit to another of the plurality of secondary station boards.

5. The analyzer system according to claim 1, wherein the network includes a plurality of network lines configured to correspond to the arrangement positions of the plurality of secondary control units and/or functions of the processing units to which the plurality of secondary control units connect.

* * * * *